United States Patent [19]

Balaban et al.

[11] 4,087,608

[45] May 2, 1978

[54] PRODUCTION OF CHLORO-S-TRIAZINE TRIONES

[75] Inventors: Stephen M. Balaban, Chesterfield, Mo.; Raymond C. Cox, Jr., Belleville, Ill.

[73] Assignee: Monsanto Company, St. Louis, Mo.

[21] Appl. No.: 812,556

[22] Filed: Jul. 5, 1977

[51] Int. Cl.$^2$ ........................................... C07D 251/36
[52] U.S. Cl. ..................................................... 544/190
[58] Field of Search ......................................... 544/190

[56] References Cited

U.S. PATENT DOCUMENTS 3,835,135  9/1974  Sawhill ................................. 544/190

Primary Examiner—John M. Ford
Attorney, Agent, or Firm—William H. Duffey

[57] ABSTRACT

Chloro-s-triazine triones having improved crystal properties are obtained by reacting cyanuric acid, alkali metal hydroxide and chlorine in an aqueous reaction mixture in the presence of a crystal modifier selected from the group consisting of alkali metal disulfonates of alkylated diphenyloxide wherein the alkyl group contains from about 8 to about 14 carbon atoms, and alkylated diphenyloxide disulfonic acid wherein the alkyl group contains from about 8 to about 14 carbon atoms.

6 Claims, No Drawings

PRODUCTION OF CHLORO-S-TRIAZINE TRIONES

BACKGROUND OF THE INVENTION

1. Field of the Invention

The present invention relates to an improved process for manufacturing chloro-s-triazine triones which are sometimes referred to as chlorocyanuric acids or chloroisocyanuric acids. More specifically, this invention pertains to a method for preparing chloro-s-triazine triones, particularly trichloro-s-triazine trione, having enhanced crystal properties.

2. Description of the Prior Art

The preparation of chloro-s-triazine triones such as trichloro-s-triazine trione or dichloro-s-triazine trione is well known in the prior art.

One method for producing chloro-s-triazine trione is described in U.S. Pat. No. 2,969,360 issued Jan. 24, 1961. In this process, cyanuric acid (also known as s-triazine trione) is fed along with aqueous alkali (in molar ratio of about one mole of caustic per atom of chlorine to be attached) and chlorine to an aqueous reaction zone which is maintained at a pH in the vicinity of 3.5. The feed ingredients are added in essentially stoichiometric proportions. The crude chloro-s-triazine trione precipitates from the solution as a solid slurry. The slurry product is continually or periodically filtered to separate the crystalline products from the mother liquor whereupon the crystalline product is dried.

Prior art processes for producing chloro-s-triazine trione have been beset with numerous difficulties attributable to deficient particle size. For example, considerable manufacturing downtime and rate variances have been experienced in the manufacture of trichloro-s-triazine trione due to difficulties in water removal which result in a slushy feed to the dryer. When very wet or slushy product material reaches the dryer it becomes necessary to reduce the production rate or shut down the unit in order to avoid packaging wet trichloro-s-triazine trione. The primary cause for this problem is believed to be the very fine particle size produced in the process.

The patent literature reports other problems attributable to small particle size such as those relating to product separation (filtration), washing and drying as well as those relating to handling of the final dusty product. Small particle size is also said to decrease product stability.

It has been proposed heretofore in U.S. Pat. No. 3,120,522 issued Feb. 4, 1964, that chloro-s-triazine trione crystals having increased size can be produced by adding to the reaction mixture from which these crystals are formed, from 50 to 1,000 ppm of a chlorinated hydrocarbon containing 1 to 6 carbon atoms and having not more than one hydrogen atom in its molecule.

It has further been proposed in U.S. Pat. No. 3,427,314 issued Feb. 11, 1969, that increased particle size can be achieved by heating trichloro-s-triazine trione to from 130° to 225° C. with agitation and thereby causing the particles to agglomerate.

In addition, it has been proposed in U.S. Pat. No. 3,453,274 issued July 1, 1969, that crystal size of chloro-s-triazine triones may be increased by adding, as a surface active agent, an alkali metal alkyl sulfate or an alkali metal alkylarylsulfonate wherein the aryl portion is phenyl or naphthyl, to the reaction mixture while maintaining a pH between 1.0 and 4.5.

U.S. Pat. No. 3,941,784, which issued Mar. 2, 1976, teaches the crystal promotion of chloro-s-triazine trione by adding to the reaction mixture a small amount of polyoxyethylene, polyoxypropylene, or polyoxyethylene-polyoxypropylene copolymers.

The principal object of the present invention is to provide a chloro-s-triazine trione product having enhanced crystal properties and exhibiting outstanding stability when formulated with other chemicals in bleaching products. This object has been accomplished through use of certain crystal modifiers.

SUMMARY OF THE INVENTION

The objects of this invention are achieved through use of certain crystal modifiers during the manufacture of chloro-s-triazine triones. These modifiers are selected from the group consisting of alkali metal disulfonates of alkylated diphenyloxide wherein the alkyl group contains from about 8 to about 14 carbon atoms, and alkylated diphenyloxide disulfonic acid wherein the alkyl group contains from about 8 to about 14 carbon atoms.

Alkali metal disulfonates are preferred over the acid form. The preferred alkali metal is sodium.

An exemplary crystal modifier which has afforded the production of trichloro-s-triazine trione crystals of outstanding clarity and chlorine stability is sodium dodecyl diphenyloxide disulfonate. Another suitable crystal modifier is sodium n-decyl diphenyloxide disulfonate. Still another modifier is dodecyl diphenyloxide disulfonic acid.

DESCRIPTION OF THE PREFERRED EMBODIMENTS

While the crystal modifiers of the present invention will be mainly described in connection with the manufacture of trichloro-s-triazine trione, their utility is not limited thereto. Superior results will likewise be seen in the manufacture of dichloro-s-triazine trione.

A preferred method of manufacturing trichloro-s-triazine trione to which this invention is applicable is to mix a slurry of substantially pure cyanuric acid with alkali metal hydroxide (e.g., sodium or potassium hydroxide, preferably the former), to prepare an aqueous solution in which the sodium hydroxide to cyanuric acid molar ratio is about 3:1. The solution is then fed continuously to a reactor to which chlorine and the crystal modifier are also fed continuously, while maintaining a temperature of the reactor contents at about 25° C. with a pH of about 3.5. Although the pH can vary between about 1.0 and 4.5, the range of 3.0 to 4.5 is preferable. The crystal modifier feed rate is adjusted to maintain a concentration of the crystal modifier in the reactor at from about 20 to 500 parts per million (ppm) by weight and preferably about 100 to 300 ppm by weight, based upon the reactor contents.

A preferred crystal modifier for use herein is sodium dodecyl diphenyloxide disulfonate. This disulfonate is commercially available. It can be obtained in liquid form as a 45-50% concentrate, for example, from Dow Chemical Company under the trade name "Dowfax 2A1".

When using sodium dodecyl diphenyloxide disulfonate as the crystal modifier in the preferred process described above, the product of the process (trichloro-s-triazine trione) is withdrawn from the reaction as a slurry, then filtered, dried and packaged. When produced in this manner, the particles of trichloro-s-triazine trione are single, clear crystals of suitable size and structural integrity to exhibit outstanding bleach stability when formulated with other chemicals in bleaching and scouring compositions. It is known that the crystal properties of chloro-s-triazine trione have substantial influence on the retention of bleaching strength in formulations containing such triones. Thus, particle size and particle clarity are important for superior bleach stability.

The exact mechanism by which the crystal modifiers of this invention achieve the superior bleach stability results is not fully understood. Thus, since the inventors herein do not wish to be bound by a single theory in explaining their unexpected results, the mechanism is merely described as one of "crystal modification" and the additive is simply called a "crystal modifier". Even though reference is made herein to "crystal size", "particle size", "crystalline product", etc., these phrases are employed for convenience of description and should not be construed as restricting the invention to any single theory.

A further understanding of the advantages and processes of the present invention will be derived from the following examples which are intended to illustrate the invention but not to limit the scope thereof, parts and percentages being by weight unless otherwise specified.

EXAMPLE 1

This Example illustrates a conventional preparation of trichloro-s-triazine trione wherein no crystal modifier or promoter is employed. A feed solution was prepared by mixing a cyanuric acid slurry with sodium hydroxide to produce a solution containing 7.6% cyanuric acid with a mole ratio of sodium hydroxide to cyanuric acid of 3.2:1. The chlorination reaction was provided for by a jacketed 1.4 liter glass reactor equipped with a stirrer, side arm for product overflow, subsurface feed tube and a fritted glass sparger. Starting with water in the reactor, feed solution is introduced through the feed tube at about 40 ml. per minute and chlorine is introduced through the sparger at about 5.5 grams per minute. The pH was controlled in the range of 3.5 to 3.8 by adjusting chlorine feed rate, and reaction temperature was controlled between 22° and 27° C. by circulating ice water through the reactor jacket. The product slurry, which overflows the side arm, is filtered to separate the crystalline product from the mother liquor, and is then dried in an oven at about 100° C. The product was observed to settle slowly and was filtered to 10 to 12% free moisture.

EXAMPLE 2

This Example was conducted in a manner identical to that of Example 1 except for the presence of a crystal promoter within the scope of aforementioned U.S. Pat. No. 3,941,784. The promoter employed was a polyoxyethylene-polyoxypropylene copolymer identified as "Pluronic L-62" and available from BASF-Wyandotte Corporation. The copolymer specific gravity is 1.03; the refractive index is 1.4550 at 25° C; and the pour point is −4° C. A feed solution identical to that of Example 1 was prepared. A chlorination was conducted as described in Example 1 except that 200 ppm (based upon the reactor contents) of polyoxyethylene-polyoxypropylene copolymer was introduced to the reaction. Part of this 200 ppm promoter addition was admitted to the initial reactor water charge and part was admitted to the feed solution. The resulting product in this case was observed to settle rapidly and was filtered to 4–5% free moisture.

EXAMPLE 3

This Example illustrates the preparation of trichloro-s-triazine trione with the aid of a crystal modifier of the present invention. Example 3 was conducted in a manner identical to that of Example 1 except for the addition of 200 ppm, based upon the reactor contents, of sodium dodecyl diphenyloxide disulfonate (as a 45% concentrate in a liquid vehicle) to the reaction vessel. The resulting trichloro-s-triazine trione product exhibited outstanding clarity in the single clear crystals which were produced.

Particle size comparisons were made on the respective dried products from Examples 1, 2 and 3 above. Apparent particle size, on a relative basis, was ascertained by observing the cumulative weight percent of product retained on a screen having a predetermined number of meshes per unit length.

The unmodified, unpromoted product of Example 1 exhibited the smallest apparent particle size. The product of Example 2, although exhibiting an apparent size greater than that of Example 3 in screen measurements, is suspected of undergoing size attrition during certain conditions of handling in compounding operations sometimes employed to formulate cleansing and bleaching compositions referred to hereafter.

It will therefore be seen from chlorine stability testing herein that apparent particle size does not of itself relate to stability.

Bleach stability of cleansing compositions containing chloro-s-triazine triones is customarily determined by measuring the percentage of available chlorine remaining in the cleansing or bleaching composition following a predetermined number of days exposure of the composition to ambient conditions. One such aging test calls for the placement of the bleaching or cleansing composition in half-filled canisters and exposing the canisters to air at 80° F. (26.7° C.) and 80% relative humidity with both open and closed tops on the canisters.

Chlorine stability results with the unpromoted, unmodified crystalline trichloro-s-triazine trione product of Example 1 were substandard and unacceptable for commercial cleansing compositions. The following Table compares the chlorine stability of the products of Example 2 and Example 3, respectively. It will be seen that the single clear crystal of the product of Example 3, although of smaller apparent particle size than that of Example 2 according to screen measurements, is nonetheless a superior product from the standpoint of chlorine stability. The data in the Table was obtained following the typical aging test described above, using open top canisters.

TABLE

| Formulation Exposure (days) | Chlorine Stability Test | |
|---|---|---|
| | Available Chlorine Remaining (%) | |
| | Example 2 | Example 3 |
| 8 | 78 | 82 |
| 10 | 69 | 79 |
| 12 | 61 | 77 |
| 14 | 54 | 74 |
| 16 | 47 | 72 |
| 18 | 40 | 70 |

In a particular cleansing formulation of the Table above, it can be seen that the sodium dodecyl diphenyloxide disulfonate crystal modifier of the present invention contributes significantly to available chlorine stability. If desired, other alkali metal disulfonates of alkylated diphenyloxide can be similarly employed. Exemplary crystal modifiers within the scope of this invention are sodium octyl diphenyloxide disulfonate; sodium nonyl diphenyloxide disulfonate; sodium n-decyl diphenyloxide disulfonate; potassium n-decyl diphenyloxide disulfonate; octyl diphenyloxide disulfonic acid; dodecyl diphenyloxide disulfonic acid; sodium tridecyl diphenyloxide disulfonate; and potassium tetradecyl diphenyloxide disulfonate.

For certain applications, dichloro-s-triazine trione may be the desired end product instead of trichloro-s-triazine trione. The former can be prepared in a manner similar to that illustrated in Example 1 except that the feed solution can be prepared by mixing a cyanuric acid slurry with sodium hydroxide to produce a solution containing about 9.8% cyanuric acid and having a sodium hydroxide to cyanuric acid mole ratio of about 2.1:1. Chlorine is typically introduced at about 7.1 grams per minute to maintain a pH in the range of 2.1 to about 2.3. It should be understood, however, that this is only one exemplification of the preparation of dichloro-s-triazine trione.

It should be further understood that the preferred concentration of the crystal modifier in the reaction vessel for the present invention for making chloro-s-triazine triones is not restricted to 20 to 500 ppm. Functionality can be achieved with these crystal modifiers at higher or lower concentrations. While less than 20 ppm concentration of the modifier based upon the reactor contents is functional, more significant results are achieved between 20 and 500 ppm. Although modifier concentrations above 500 ppm would produce satisfactory crystal properties, not enough improvement would be expected to offset the economic disadvantages of the surplus presence of modifier.

In adapting the process of this invention to certain continuous manufacturing operations, it may be desirable to introduce the modifier directly to the chlorinator and not to the feed solution in order to increase the efficiency of the modifier. It may also be desirable to provide careful control of drying conditions such that the effect of the modifier will not be diminished due to particle overheating or other known undesirable occurrences. It is known, for example, that trichloro-s-triazine trione exhibits a significant temperature dependence during the drying step. Desirably, trichloro-s-triazine trione should not be dried at temperatures which will cause the particles to exceed about 130° C.

An abrupt absorption of heat into the trichloro-s-triazine trione particle is usually observed when the particle temperature during the drying step is allowed to exceed about 130° C. The phenomenon associated with this temperature is sometimes referred to as a "phase change". Exceeding 130° C. particle temperature during drying of trichloro-s-triazine trione is generally accompanied by a reduced density of the dried particle after cooling. Furthermore, the reduced density of the particle after cooling is characterized by extension of the lattice in the crystalline structure of the particle. It is therefore desirable to conduct the drying step associated with the process of this invention in a manner which maintains particle temperature during drying between about 80° C. and about 120° C., preferably about 95° to about 105° C.

It may be desirable to introduce certain antifoaming agents during a continuous manufacturing process in order to offset any tendencies of these crystal modifiers to generate foam.

While this invention has been described with respect to specific examples and embodiments, it is to be understood that the invention is not limited thereto and that it can be variously practiced within the scope of the following claims.

The embodiments of this invention in which an exclusive property or privilege is claimed are defined as follows:

1. In a process for preparing a chloro-s-triazine trione selected from the group consisting of dichloro-s-triazine trione, trichloro-s-triazine trione and mixtures thereof by the reaction of cyanuric acid with an alkali metal hydroxide and chlorine in an aqueous reaction mixture and recovering the chloro-s-triazine trione product from said reaction mixture, the improvement which comprises conducting the reaction in the presence of a crystal modifier selected from the group consisting of alkali metal disulfonates of alkylated diphenyloxide wherein the alkyl group contains from about 8 to about 14 carbon atoms, and alkylated diphenyloxide disulfonic acid wherein the alkyl group contains from about 8 to about 14 carbon atoms.

2. A process of claim 1 wherein the crystal modifier concentration is from 20 to about 500 parts per million by weight based upon the reactor contents.

3. A process of claim 1 wherein the alkali metal hydroxide is sodium hydroxide.

4. A process of claim 1 wherein the crystal modifier is a sodium disulfonate of alkylated diphenyloxide.

5. A process of claim 1 wherein the crystal modifier is sodium dodecyl diphenyloxide disulfonate, sodium n-decyl diphenyloxide disulfonate, or dodecyl diphenyloxide disulfonic acid.

6. In a process for preparing trichloro-s-triazine trione by the reaction of cyanuric acid with sodium hydroxide and chlorine in an aqueous reaction mixture and recovering the trichloro-s-triazine trione product from said reaction mixture, the improvement which comprises conducting the reaction in the presence of from about 20 to about 500 parts per million by weight of sodium dodecyl diphenyloxide disulfonate, based upon the reactor contents.

* * * * *